United States Patent [19]

Southard et al.

[11] Patent Number: 5,013,553

[45] Date of Patent: May 7, 1991

[54] DRUG DELIVERY DEVICES

[75] Inventors: G. Lee Southard; Ronald J. Harkrader, both of Fort Collins, Colo.

[73] Assignee: Vipont Pharmaceutical, Inc., Fort Collins, Colo.

[21] Appl. No.: 400,561

[22] Filed: Aug. 29, 1989

Related U.S. Application Data

[63] Continuation of Ser. No. 68,251, Jun. 30, 1987, abandoned.

[51] Int. Cl.$^5$ .......................... A61K 7/26; A61K 6/00; A61F 2/00
[52] U.S. Cl. .................... 424/426; 424/435; 424/78; 424/195.1; 424/58; 514/900
[58] Field of Search ................... 424/426, 49, 58, 435; 514/900, 902

[56] References Cited

U.S. PATENT DOCUMENTS

| | | | |
|---|---|---|---|
| 4,406,881 | 9/1983 | Ladanyi | 424/49 |
| 4,515,771 | 7/1985 | Fine | 424/52 |
| 4,568,535 | 2/1986 | Loesche | 424/435 |
| 4,599,228 | 7/1986 | Ladanyi | 424/52 |
| 4,685,883 | 8/1987 | Jernberg | 424/435 |
| 4,722,948 | 2/1988 | Sanderson | 523/115 |
| 4,764,377 | 8/1988 | Goodson | 424/435 |
| 4,780,320 | 10/1988 | Baker | 424/493 |

OTHER PUBLICATIONS

Isoquinoline Alkaloids in Local Periodontal Disease Therapy, Cerna et al., 1984, pp. 159-162.

Primary Examiner—Thurman K. Page
Assistant Examiner—James M. Spear
Attorney, Agent, or Firm—Merchant, Gould, Smith, Edell, Welter & Schmidt

[57] ABSTRACT

Drug delivery devices and techniques are described for use in treatment of periodontal disease and the like. The delivery device includes benzo (c) phenanthridine alkaloid in a bioerodable and biocompatible material. The alkaloid is slowly released from the bioerodable material in the oral cavity. The bioerodable material may be polymeric and may be natural or synthetic. The delivery device may be inserted subgingivally (e.g., in a periodontal pocket) where the alkaloid is released slowly over a period of days.

28 Claims, 1 Drawing Sheet

FORM I

FORM II

DRUG DELIVERY DEVICES

This is a continuation of application Ser. No. 068,251, filed on June 30, 1987, now abandoned.

FIELD OF THE INVENTION

This invention relates to devices and techniques for delivering drugs to a localized site. More particularly, this invention relates to devices and techniques for delivering drugs to a site in the oral cavity. Even more particularly, this invention relates to treatment of periodontal tissues with benzophenanthridine alkaloids.

BACKGROUND OF THE INVENTION

Periodontal disease is a common and widespread disease which has been shown to be a result of pathogenic bacterial infection established within the gingival sulcus. This condition, if not arrested, will deepen to cause formation of a periodontal pocket. The bacteria found in the periodontal pocket are more anaerobic and contain more gram negative organisms than bacteria found supragingivally.

It is known that several factors prevent or impede the treatment of periodontal disease by supragingival application of drugs or other medicaments. For example, the close proximity of the gum tissue to a tooth impairs diffusion of a medicament into a periodontal pocket. Also, a gingival fluid is continually produced in the pocket and flows outwardly. This fluid flows at a rate of about 1 to 5 microliters per hour in healthy periodontal tissues and at a rate of about 10 to 100 microliters per hour in diseased periodontal tissue.

As a result, the penetration of topically or supragingivally applied medicaments has been largely ineffective in the treatment of periodontal disease. Topical application of medicaments typically does not result in penetration of more than 2 mm. into a periodontal pocket. Since periodontal pockets can be about 5 mm. in depth, topical application does not provide any effective means for treatment.

Systematic application of drugs such as tetracycline to periodontal tissue for treatment of the disease is known. Metronidazole on a film of ethylcellulose has been placed in a periodontal pocket for a period of days during which the active agent is slowly released. Then the film must be removed. It is not bioerodible. See U.S. Pat. No. 4,568,535.

Other techniques have also been proposed for treatment of periodontal disease, e.g., capsules or tablets held in the mouth like a throat lozenge, buccal implants, bandages and dressings, topically applied compositions, fibers, dental floss, etc. These techniques, however, are not effective in penetrating the periodontal pocket.

It has also been proposed to insert medicament-impregnated strings or fibers into periodontal pockets to treat the disease. See, for example, U.S. Pat. Nos. 4,406,881 and 4,599,228, incorporated herein by reference. The use of strings or fibers may not result in uniform treatment of the tissue and must be removed by the dentist again at the desired time. These patents also refer to the use of an undiluted paste for treatment of periodontal tissue, the paste being left in place for 10–15 minutes and then removed.

It is also known to use systemic antibiotic treatment to try to control specific pathogenic species. However, use of this treatment results in low concentrations of antibiotic at the site of the periodontal pathogens.

Conventional therapy and treatment of periodontal disease in humans involves the mechanical removal of bacterial plaques and accumulations from the periodontal pocket, often called root planing and scaling. More severe cases may require periodontal surgery to remove damaged tissue. These procedures are expensive, painful, cause extensive bleeding and general discomfort. These procedures are also temporary at best, and frequent recall visits to the dental surgeon are often necessary.

SUMMARY OF THE PRESENT INVENTION

In accordance with the present invention there is provided a bioerodable delivery device which is especially useful in the treatment of periodontal disease. The bioerodable delivery device comprises:

(a) bioerodable, biocompatible material; and (b) benzo (c) phenanthridine alkaloid.

The alkaloid is releasably contained in the bioerodable material in a manner such that the alkaloid is slowly released from the bioerodable material in the oral cavity.

The delivery device is formable and can be placed into and retained in a periodontal pocket to be treated. The alkaloid slowly releases from the bioerodable material in a manner such that an effective concentration of the alkaloid in the pocket is maintained for a period of several days (e.g., 7–14 days).

The techniques of the invention are useful generally for the treatment of periodontal infections such as periodontitis and irritated gums such as gingivitis. These diseases occur below the gingival margin in the periodontal pocket or along the gum line.

The delivery device bioerodes or bioabsorbs slowly in the periodontal pocket. This allows slow release of the alkaloid into the pocket over a period of several days (e.g., 10 to 14 days). In this manner the alkaloid reduces periodontal pathogenic bacteria (such as Bacteroides gingivalis and many other types of bacteria) and also reduces inflammation.

The bioerodable material is typically polymeric (natural or synthetic). It is biocompatible and preferably is bioabsorbable. It is also non-toxic, non-carcinogenic, and causes no adverse immunologic response. Because the material is bioerodable, the dentist does not have to remove the material after the alkaloid has been released in the periodontal pocket. The amount of alkaloid present in the bioerodable material may vary over a broad range.

The alkaloid may be present in various forms. For example, it may be present as the iminium ion, or as a salt, or as an alkanolamine, alcoholate, or hydroxylate. The alkaloid is an antimicrobial agent, an anti-inflammatory agent, and it also inhibits calcium loss from bone.

The drug delivery devices described herein can be applied to a patient subgingivally by a dental professional using conventional equipment. No strings, fibers or films are used which must be wrapped around a tooth. When the delivery device is in the form of a gel or viscous liquid it may be inserted into the periodontal pocket by means of a syringe. The procedure may be performed rapidly and efficiently. The material penetrates to the bottom of the periodontal pocket so that the anerobes in the pocket are exposed to the alkaloid as it is released.

Another advantage of the deliver devices of this invention is that they can be provided in any desired physical form. Solid forms also can be made in any size (e.g., to fit a particular pocket size or shape) and are pliable and conformable so that they will conform to the shape of the pocket. The material can be adhesive, if desired, so as to adhere to the tissues. It remains in the periodontal pocket and is not dislodged by crevicular fluid flow.

Also, the use of the alkaloid in the alkanolamine form serves as a controlled release pro-drug.

Other advantages will be apparent from the following detailed description.

Brief Description of the Drawings

The invention is described in more detail hereinafter with reference to the accompanying drawings, wherein like reference characters refer to the same parts throughout the several views and in which.

DETAILED DESCRIPTION OF THE INVENTION

Figure 1A:
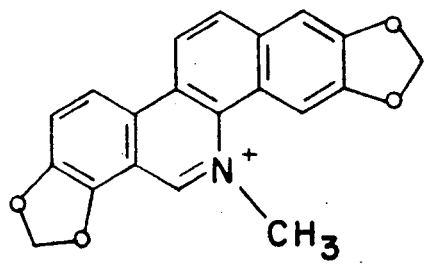
FIG. 1 shows the iminium ion (Form I) of sanguinarine and also the alkanolamine form (Form II) of sanguinarine.
Figure 1B:
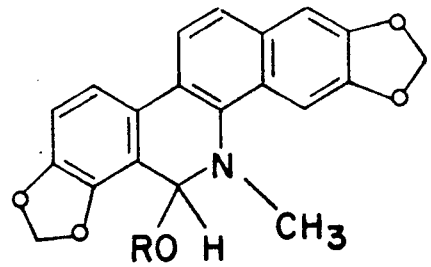
Figure 2:
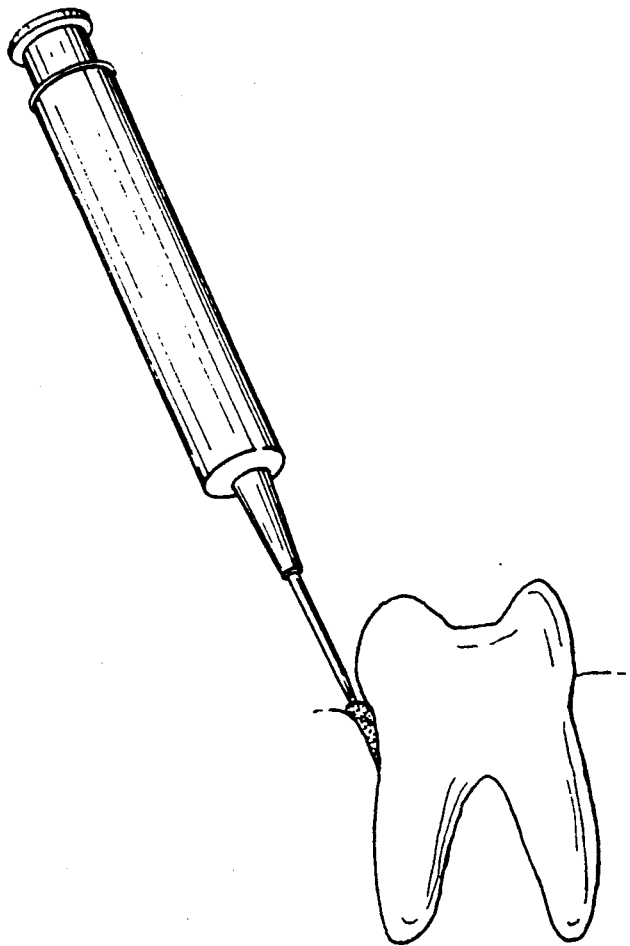
FIG. 2 illustrates the injection of a gel or viscous liquid form of delivery device into a periodontal pocket adjacent a tooth.
Figure 3:
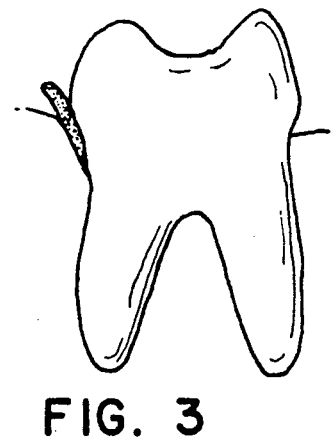
FIG. 3 shows a solid or semi-solid form of delivery device in a periodontal pocket adjacent a tooth.

The bioabsorbable delivery device of this invention includes bioerodable and biocompatible material and a benzo (c) phenanthridine alkaloid. The delivery device is formable so that it can be placed within a periodontal pocket and will generally conform to the periodontal tissue and the shape of the pocket. The delivery device may be a solid plastic mass or it may be in the form of a gel, viscous liquid, semi-solid, etc. It may also be adhesive so that it will become adhered to the tissue.

The bioerodable material is typically polymeric (natural or synthetic). Preferably it is bioabsorbable in the oral cavity. Representative useful materials include: polylactides; polyglycolides; polycaprolactones; polyanhydrides; pyrollidones (e.g., methylpyrollidone); cellulosic polymers (e.g., carboxymethyl cellulose); methacrylates; collagen (e.g., gelatin), and glycerin. Mixtures and combinations of these may also be used.

Particularly useful bioerodable polymers include polylactides having a molecular weight less than about 4000 and an inherent viscosity less than about 0.4 in chloroform at 25° C. Also useful are polylactide/glycolide copolymers having a molecular weight less than about 4000 and an inherent viscosity less than about 0.5 in chloroform at 25° C. Copolymers of polylactide/caprolactone having a molecular weight less than about 4000 are also useful.

The benzo (c) phenanthridine alkaloid may be of various types. For example, useful alkaloids include sanguinarine, sanguirubine, sanguilutine, chelirubine, chelerythrine, and chelilutine. The alkaloid may be in the iminium ion form, or a salt (e.g., sulfate, nitrate, or chloride), or alkanolamine, alcoholate, hydroxylate, acetate, citrate, and tartrate. Mixtures of these may also be used.

The amount of alkaloid present in the delivery device may vary, for example, from about 1-80% by weight. The amount of bioerodable material used may also vary, for example, from about 20-99%. Preferably the alkaloid is present at a concentration of about 1-50%, with a concentration of 10-50% being more preferred. Preferably it is uniformly distributed in the bioerodable material.

The alkaloid slowly releases from the bioerodable material in the oral cavity so as to maintain an effective concentration of the alkaloid in the periodontal pocket for a period of several days. This is much more effective than a simple application of alkaloid alone to the pocket. The amount of alkaloid released in a pocket can be predetermined so that exactly the desired amount is released over the desired time period. In this manner the amount of alkaloid present can be controlled. Assuming an average pocket size of about 250 microliters, it is preferable to place a delivery device therein which contains about 500 micrograms of alkaloid.

Preferably the alkaloid is released from the bioerodable material at a rate in the range of about 30 to 100 micrograms per day. A rate of about 100 micrograms per day is most preferred.

The bioerodable material preferably erodes or is absorbed within about 30 days. Thus, so long as the alkaloid is released in the pocket within about 14 days, it is permissible for the bioerodable material to take a longer period (e.g., up to about 30 days) to be eroded or absorbed.

The bioerodable delivery device of the invention is useful in both animal and human subjects. Examples of animal subjects include dogs, cats and other animals (e.g., monkeys) which may be affected by periodontal disease.

It is preferable to include an antioxidant in the delivery devices. The amount of antioxidant present may vary from about 0.1 to 1% by weight. Useful antioxidants include glutathione, ascorbic acid or other such compounds, e.g. BHT (butylated hydroxy toluene). The presence of antioxidant inhibits the oxidation of alkaloid in the periodontal pocket.

The alkaloid may be soluble or miscible in the bioerodable material, although this is not absolutely required so long as the alkaloid is slowly released from the bioerodable material in the periodontal pocket over a period of about 7-21 days, preferably 10 to 14 days. For example, sanguinarine ethanolate may be dispersed and suspended in glycerine or water and then injected into the periodontal pocket by means of a syringe (e.g., with an 18 or 22 gauge needle).

The alkaloids described herein can be obtained from Papaveraceae plants such as *Sanguinaria canadensis, Macleaya cordata, Corydalis sevctvozii, C. ledebouni, Chelidonium majus, Escholtzia,* and others. Purification of these alkaloids is described, e.g., in U.S. Pat. No. 4,145,412, incorporated herein by reference.

Other isolation procedures require isolation of the alkaloid fraction using a mineral acid and a low molecular weight alcohol (e.g., methanol, ethanol, isopropanol, or other low molecular weight alcohols containing up to 5 carbons), chloroform or methylene chloride, precipitation of the alcohol or solvent fraction using a base, dissolution in water, and precipitation with an acid and a salt such as sodium chloride. The sample is dried and the precipitate is dissolved in an alcohol, ethyl acetate, or methylene chloride and then applied to a silica column. Fractions are eluted with ethyl acetate and methanol (ranging from 0% to 100% methanol in ethyl acetate). The impure alkaloid fractions are precipitated and applied to a Florisil column, eluting with methylene chloride or chloroform. The fractions are recrystallized in a mineral acid and methanol after removing the methylene chloride or chloroform by evaporation.

The sanguilutine and chelerythrine alkaloids are isolated as essentially pure components (i.e., greater than 95% purity). Sanguirubine, chelilutine, and chelirubine require an additional silica clean-up to purify them.

Preparation of sanguinarine is also described in J. Natural Products, Vol. 49, No. 6, pp. 1109-11 (1986), incorporated herein by reference. Sanguinarine chloride is also commercially available from Aldrich Chemical under catalog #30745-9.

It is well known in periodontal literature that the absence of black pigmented bacteroides and spirochetes is associated with periodontal health. An increase in these organisms is associated with periodontal disease. Antimicrobial agents which suppress these microbes have a therapeutic value for the treatment of periodontitis. Previous in vitro studies have shown the following minimum inhibitory concentration (MIC) for anerobes found in the periodontal pocket.

|  | Sanguinarine MIC (ug/ml) |
| --- | --- |
| *Actinobacillus actinomycetemcomitans* | 8–16 |
| *Bacteroides gingivalis* | 2 |
| *Bacteroides melaninogenicas* | 8 |
| *Bacteroides oralis* | 8 |
| *Wolinella recta* | 4 |
| *Eikenella corrodens* | 16 |
| *Fusobacterium nucleatum* | 4 |
| *Caprocytophaga gingivalis* | 4 |

The drug delivery devices of this invention are useful in controlling these bacteria in the periodontal pocket. The alkaloids also inhibit calcium loss from bone. Further, the alkaloids serve as anti-inflammation agents.

The delivery devices and techniques of the invention are further illustrated by means of the following examples:

EXAMPLE 1

Sanguinarine chloride (0.2 grams) is added to 2.5 grams of gelatin which has been dissolved in deionized water. The resulting solution is treated with 2 ml. of phosphate buffered saline and then added at 60° C. to a solution comprising 20 ml. of petroleum ether and 80 ml. of heavy mineral oil and then stirred vigorously. After the beaker was cooled to 40° C. the solid product was removed and washed with 50/50 petroleum ether/diethyl ether. The gelatin particles are sized through a nylon mesh screen (less than about 25 microns).

A 0.07 g. sample of the gelatin was suspended in 50 ml. of isotonic saline and held at 37° C. The gelatin was completely dissolved in three days, and the saline solution contained 89 mg./ml. or 4,450 mg. of sanguinarine chloride in the 50 ml. of saline, as measured by high performance liquid chromatography.

EXAMPLE 2

A 0.07 gram sample containing 98% sanguinarine chloride was added to 2.9 grams of USP glycerin. The resulting mixture was added to 100 ml. of isotonic saline. The amount of sanguinarine chloride released into the saline was determined by high performance liquid chromatography. The following Table 1 shows the results obtained.

TABLE 1

| Time (Hours) | Sanguinarine Chloride (μg/ml in Saline) | Total Sanguinarine Chloride (μg) |
| --- | --- | --- |
| 1 | 33.7 | 3,370 |
| 18 | 149.2 | 14,920 |
| 72 | 198.8 | 19,880 |

TABLE 1-continued

| Time (Hours) | Sanguinarine Chloride (μg/ml in Saline) | Total Sanguinarine Chloride (μg) |
| --- | --- | --- |
| 168 | 274.7 | 27,470 |

EXAMPLE 3

A 0.06 gram sample of sanguinarine ethanolate was prepared by dissolving sanguinarine chloride in ethanol and raising the pH to 8 with ammonium hydroxide. The insoluble precipitate was analyzed by NMR and ultraviolet spectrophotometry and determined to be sanguinarine ethanolate.

The product was then suspended in 2.9 grams of USP glycerin and added to a flask containing 100 ml. of isotonic saline. The amount of sanguinarine released into the saline was determined by high performance liquid chromatography. The sanguinarine ethanolate released the sanguinarine into the saline in the iminium ion form. The results are shown in Table 2.

TABLE 2

| Time (Hours) | Sanguinarine (μg/ml in Saline) | Total Sanguinarine (μg) |
| --- | --- | --- |
| 1 | 3.1 | 310 |
| 18 | 11.1 | 1,110 |
| 168 | 15.4 | 1,540 |

EXAMPLE 4

A 0.25 gram sample of the sanguinarine ethanolate prepared in accordance with Example 3 was mixed with 2.25 grams of polycaprolactone diol (mol. wt. 2000; commercially available from Scientific Polymer Products, Inc., Ontario, N.Y.) in methylene chloride. The mixture was stirred under all of the components were in solution, after which the solution was dried under vacuum to remove all of the methylene chloride.

A 0.1 gram of the resulting product was placed into a 100 ml. sample of isotonic saline. The sanguinarine ethanolate diffused into the isotonic saline as the iminium ion form. The amount of sanguinarine in the saline was determined by high performance liquid chromatography. The isotonic saline solution was changed every 72 hours. The results are shown in Table 3.

TABLE 3

| Time (Hours) | Sanguinarine (μg/ml in Saline) | Total Sanguinarine (μg) |
| --- | --- | --- |
| 2 | 1.6 | 160 |
| 24 | 2.6 | 260 |
| 48 | 15.6 | 1,560 |
| 72 | 36.0 | 3,600 |
| 120 | 36.8 | 3,680 |
| 240 | 31.2 | 3,120 |

EXAMPLE 5

A 0.80 gram sample of poly-d,1-lactide MW2000 (commercially available from Boerhinger-Ingelheim) was added to methylene chloride with stirring to dissolve the polymer. Then 0.20 gram of sanguinarine ethanolate are added to the polymer/methylene chloride solution. After the sanguinarine ethanolate is dissolved the mixture is dried under vacuum to remove the methylene chloride.

A 100 mg. sample of the polymer-sanguinarine ethanolate product is placed into a 100 ml. sample of isotonic saline at 37° C. The sanguinarine ethanolate is released from the polymer into the saline as the iminium ion form. Analysis of the saline by high performance liquid chromatography showed the results given in Table 4.

TABLE 4

| Time (Hours) | Sanguinarine (μg/ml in Saline) | Total Sanguinarine (μg) |
|---|---|---|
| 1 | 6.6 | 660 |
| 24 | 18.1 | 1,810 |
| 48 | 14.2 | 1,420 |
| 96 | 13.1 | 1,310 |
| 120 | 14.8 | 1,480 |
| 144 | 17.6 | 1,760 |
| 168 | 23.7 | 2,367 |
| 192 | 60.8 | 6,005 |
| 216 | 62.0 | 6,200 |

The saline solution was changed every 72 hours.

EXAMPLE 6

A 0.40 gram sample of poly-1-lactide MW 2000 (commercially available from Boerhinger-Ingelheim) and 0.040 sample of the polycaprolactone polymer described in Example 4 were mixed in methylene chloride. A 0.20 gram sample of sanguinarine ethanolate was added, after which the methylene chloride was evaporated under vacuum. The dried polymer-sanguinarine ethanolate (0.1 gram) was placed in 100 ml. of isotonic saline at 37° C. Analysis by high performance liquid chromatograph showed the results given in Table 5.

TABLE 5

| Time (Hours) | Sanguinarine (μg/ml in Saline) | Total Sanguinarine (μg) |
|---|---|---|
| 1 | 5.5 | 550 |
| 24 | 47.5 | 4,750 |
| 48 | 73.0 | 7,300 |
| 72 | 87.1 | 8,710 |
| 96 | 19.7 | 1,970 |
| 120 | 40.6 | 4,060 |
| 144 | 69.9 | 6,990 |
| 168 | 19.9 | 1,990 |
| 192 | 31.6 | 3,160 |
| 216 | 34.0 | 3,400 |

Saline was changed every 72 hours.

EXAMPLE 7

A 0.2 gram sample of poly-1-lactide is dissolved in methylene chloride or chloroform and a 0.80 gram sample of sanguinarine ethanolate is added. The resulting solution is evaporated to dryness under vacuum. The polymer/sanguinarine ethanolate (0.1 gram) is placed into 100 ml. of isotonic saline at 37° C. The sanguinarine ethanolate released into the saline as the sanguinarine iminium ion form. Analysis by high performance liquid chromatography showed the concentration of sanguinarine in the saline listed in Table 6.

TABLE 6

| Time (Hours) | Sanguinarine (μg/ml in Saline) | Total Sanguinarine (μg) |
|---|---|---|
| 1 | 5.6 | 560 |
| 24 | 27.5 | 2,750 |
| 48 | | |
| 72 | | |
| 96 | 37.2 | 3,720 |
| 120 | | |
| 144 | | |
| 168 | 83.6 | 8,360 |
| 192 | 97.5 | 9,750 |
| 216 | 131.4 | 13,140 |
| 240 | 134.7 | 13,470 |

EXAMPLE 8

High Performance Liquid Chromatography Assay for Benzo (c) Phenanthridine Alkaloid Release from Biodegradable Polymers In Vitro and In Vivo Samples (0.1 gram) of the polymer containing from 1-80% benzophenanthridine alkaloid by weight were immersed into 100 ml. isotonic saline at 37° C. in a water bath. A 5 ml. aliquot of the solution was removed periodically and assayed for the alkaloid by the following high performance liquid chromatography (HPLC) method.

A 5CN 10u radial pack column (5 mm. ID × 100 mm.; from Water Associates) was run at 0.5 ml./min. with a mobile phase containing 84/16 (u/v) methanol: water with 0.005 M. triethylamine and phosphoric acid (pH 4.8). Detection of the benzophenanthridine alkaloid was monitored at 280 nm. using sanguinarine in methanol as a standard. After removal of the 5 ml. samples, the fluid was replaced with 5 ml. of isotonic saline. A 20 μl. sample was injected into the HPLC and analyzed.

The assay for benzophenanthridine alkaloid in gingival crevicular fluid from the bioerodable polymer was taken by an intracrevicular sampling technique using filter paper strips (Harco perio paper). The relative volume of the sample is determined by a change in the dielectric constant of the filter paper (Harco periotron) and the volume was computed from a standard response. Serum is generally used as the standard since gingival crevicular fluid is very close to serum. The amount of benzophenanthridine alkaloid was determined by diluting the sample to 1 ml. and analyzing by HPLC.

EXAMPLE 9

0.100 grams of sanguilutine ethanolate was mixed with 0.900 grams of polycaprolactone diol (MW2000 Scientific Products, Inc., Ontario, N.Y.) in methylene chloride. The mixture was stirred until all of the components were in solution. The solution was dried under vacuum until all of the methylene chloride had been removed.

A 0.1 gram sample of the polymer/sanguilutine ethanolate was placed into 100 ml. of isotonic saline at 37° C. The sanguilutine ethanolate released into the saline as the iminium ion form. Analysis of the sanguilutine by high performance liquid chromatography gave the release data shown in Table 7.

TABLE 7

| Time (Hours) | Sanguilutine (μg/g) | Total Sanguilutine into saline (μg) | % Sanguilutine Released |
|---|---|---|---|
| 1 | 1.7 | 170 | 1.7 |
| 24 | 15.1 | 1.500 | 15.1 |
| 72 | 18.0 | 1.800 | 18.0 |
| 96 | 24.2 | 2,420 | 24.2 |

EXAMPLE 10

A 0.07 gram sample of Sanguinaria Extract containing the benzophenanthridine alkaloids (chelirubine, sanguinarine, sanguirubine, chelerythrine, chelilutine, and sanguilutine) were converted to their ethanolate form and added to 0.92 grams of poly d, 1-lactide (MW2000 Boerhringer-Ingerheim) in methylene chloride after all the components had gone into solution. The methylene chloride was then evaporated under vacuum.

A 0.1 gram sample of the poly d,1-lactide polymer/Sanguinaria Extract was placed into 100 ml. of isotonic saline at 37° C. The extract eluted into the saline as the iminium ion form. Analysis by HPLC showed the following release:

TABLE 8

| Time (Hours) | Total Alkaloid (μg/ml) | Total Alkaloid (μg) | % Total Alkaloid Release |
|---|---|---|---|
| 1 | 2.9 | 290 | 6.4 |
| 24 | 8.0 | 820 | 17.8 |
| 48 | 7.5 | 750 | 16.7 |
| 72 | 17.2 | 1,720 | 38.2 |
| 96 | 23.1 | 2,310 | 51.3 |
| 120 | 25.3 | 2,530 | 56.1 |
| 144 | 28.0 | 2,800 | 62.2 |
| 168 | 30.9 | 3,090 | 68.6 |
| 216 | 37.1 | 3,710 | 82.2 |

What is claimed is:

1. A bioerodable composition suitable for placement subgingivally in a periodontal pocket, said composition comprising:
   (a) bioerodable, biocompatible, sustained release, polymeric material; and
   (b) an active agent consisting essentially of a benzophenanthridine alkaloid;
wherein said alkaloid is releasably contained in said material in a manner such that said alkaloid is slowly released from said composition so as to maintain an effective concentration of said alkaloid for a period of several days in said pocket; wherein said alkaloid is present in said composition in an amount of at least 1% by weight; and wherein an aliquot of said composition suitably sized for the periodontal pocket and containing 500 micrograms of said alkaloid has a release rate in the range of about 30 to 100 micrograms per day.

2. A composition in accordance with claim 1, wherein said alkaloid is present in an amount of about 1 to 80% by weight and, correspondingly, said material is present in an amount of about 99 to 20% by weight.

3. A composition in accordance with claim 1, wherein said biocompatible material is bioabsorbable.

4. A composition in accordance with claim 1, wherein said biocompatible material is selected from the group consisting of polylactides, polyglycolides, polycaprolactones, polyanhydrides, and mixtures thereof.

5. A composition in accordance with claim 1, wherein said alkaloid is selected from the group consisting of sanguinarine, sanguirubine, sanguilutine, chelirubine, chelerythrine, and chelilutine.

6. A composition in accordance with claim 5, wherein said alkaloid is in the iminium ion form.

7. A composition in accordance with claim 5, wherein said alkaloid is selected from the group consisting of alkanolamine, alcoholate, hydroxylate, sulfate, nitrate, chloride, acetate, citrate, and tartrate.

8. A method for treating periodontal disease in a subject comprising applying to said subject, subgingivally in a periodontal pocket, a bioerodable composition comprising:
   (a) bioerodable, biocompatible, sustained release, polymeric material; and
   (b) an active agent consisting essentially of a benzophenanthridine alkaloid;
wherein said alkaloid is releasably contained in said material in a manner such that said alkaloid is slowly released from said composition so as to maintain an effective concentration of said alkaloid for a period of several days in said pocket; wherein said alkaloid is present in said composition in an amount of at least 1% by weight; and wherein an aliquot of said composition suitably sized for the periodontal pocket and containing 500 micrograms of said alkaloid has a release rate in the range of about 30 to 100 micrograms per day.

9. A method in accordance with claim 8, wherein said alkaloid is present in an amount of about 1 to 80% by weight and, correspondingly, said material is present in an amount of about 99 to 20% by weight.

10. A method in accordance with claim 8, wherein said biocompatible material is bioabsorbable.

11. A method in accordance with claim 8, wherein said biocompatible material is selected from the group consisting of polylactides, polyglycolides, polycaprolactones, polyanhydrides, and mixtures thereof.

12. A method in accordance with claim 8, wherein said alkaloid is selected from the group consisting of sanguinarine, sanguirubine, sanguilutine, chelirubine, chelerythrine, and chelilutine.

13. A method in accordance with claim 8, wherein said subject is human.

14. A method in accordance with claim 8, wherein said subject is an animal.

15. A method for treating bacterial infections in periodontal tissues comprising applying to said tissues, subgingivally, a composition comprising:
   (a) bioerodable, biocompatible, sustained release, polymeric material; and
   (b) an active agent consisting essentially of a benzophenanthridine alkaloid;
wherein said alkaloid is releasably contained in said material in a manner such that said alkaloid is slowly released from said composition so as to maintain an effective concentration of said alkaloid for a period of several days in said tissues; wherein said alkaloid is present in said composition in an amount of at least 1% by weight; and wherein an aliquot of said composition suitably sized for a periodontal pocket and containing 500 micrograms of said alkaloid has a release rate in the range of about 30 to 100 micrograms per day.

16. A method in accordance with claim 15, wherein said alkaloid is present in an amount of about 1 to 80% by weight and, correspondingly, said material is present in an amount of about 99 to 20% by weight.

17. A method in accordance with claim 15, wherein said biocompatible material is selected from the group consisting of polylactides, polyglycolides, polycaprolactones, polyanhydrides, and mixtures thereof.

18. A method in accordance with claim 15, wherein said alkaloid is selected from the group consisting of sanguinarine, sanguirubine, sanguilutine, chelirubine, chelerythrine, and chelilutine.

19. A method in accordance with claim 15, wherein said alkaloid comprises sanguinarine ethanolate.

20. A method in accordance with claim 15, wherein said alkaloid is in the iminium ion form.

21. A method in accordance with claim 15, wherein said alkaloid is selected from the group consisting of alkanolamine, alcoholate, hydroxylate, sulfate, nitrate, chloride, acetate, citrate, and tartrate.

22. A method for treating inflammatory infections in periodontal tissues in a subject comprising applying to said subject, subgingivally, a composition comprising:
   (a) bioerodable, biocompatible, sustained release material; and
   (b) an active agent consisting essentially of a benzophenanthridine alkaloid;
wherein said alkaloid is releasably contained in said material in a manner such that said alkaloid is slowly released from said composition so as to maintain an effective concentration of said alkaloid for a period of several days adjacent to said tissues; wherein said alkaloid is present in said composition in an amount of at least 1% by weight; and wherein an aliquot of said composition suitably sized for a periodontal pocket and containing 500 micrograms of said alkaloid has a release rate in the range of about 30 to 100 micrograms per day.

23. A composition according to claim 1 wherein an effective concentration of the alkaloid is maintained for a period of 7 to 14 days.

24. A composition according to claim 4 wherein the bioerodable, biocompatible material comprises a polylactide.

25. A method for treating periodontal disease according to claim 8 wherein an effective concentration of the alkaloid is maintained for a period of 7 to 14 days.

26. A method for treating periodontal disease according to claim 11 wherein the bioerodable, biocompatible material comprises a polylactide.

27. A method for treating bacterial infections in periodontal tissue according to claim 15 wherein an effective concentration of the alkaloid is maintained for a period of 7 to 14 days.

28. A method for treating bacterial infections in periodontal tissue according to claim 17 wherein the bioerodable, biocompatible material comprises a polylactide.

* * * * *

UNITED STATES PATENT AND TRADEMARK OFFICE
CERTIFICATE OF CORRECTION

PATENT NO. : 5,013,553

DATED : 05/07/91

INVENTOR(S) : Southard et al.

It is certified that error appears in the above-identified patent and that said Letters Patent is hereby corrected as shown below:

In column 3, lines 24 and 25, "DETAILED DESCRIPTION OF THE INVENTION" should read as a heading, not as a continuation in a sentence.

In column 6, line 37, "under" should read --until--.

In column 9, line 25, after "Table 8" insert --Other variants are possible without departing from the scope and spirit of the present invention--.

Signed and Sealed this

Twenty-second Day of December, 1992

Attest:

DOUGLAS B. COMER

*Attesting Officer*     *Acting Commissioner of Patents and Trademarks*